(12) United States Patent
Andreacchi et al.

(10) Patent No.: US 8,323,459 B2
(45) Date of Patent: Dec. 4, 2012

(54) AUTOMATED ELECTROPOLISHING PROCESS

(75) Inventors: Anthony S. Andreacchi, San Jose, CA (US); Andreina P. Gomez, Santa Clara, CA (US); Han Juanta, Milpitas, CA (US); Jessie Madriaga, San Jose, CA (US); Dan Joel Dirilo, Union City, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 1240 days.

(21) Appl. No.: 12/100,991

(22) Filed: Apr. 10, 2008

(65) Prior Publication Data

US 2009/0255827 A1 Oct. 15, 2009

(51) Int. Cl.
C25D 17/00 (2006.01)
B23H 3/00 (2006.01)
B23H 7/00 (2006.01)
B23H 3/04 (2006.01)

(52) U.S. Cl. ........ 204/199; 204/198; 204/212; 204/213; 204/286.1; 205/640; 205/686

(58) Field of Classification Search ........................ None
See application file for complete search history.

(56) References Cited

U.S. PATENT DOCUMENTS

| 6,183,353 B1 | 2/2001 | Frantzen |
| 6,375,826 B1 | 4/2002 | Wang et al. |
| 6,599,415 B1 | 7/2003 | Ku et al. |
| 6,679,980 B1 | 1/2004 | Andreacchi |
| 7,252,746 B2 | 8/2007 | Schaeffer |
| 7,498,062 B2 | 3/2009 | Calcaterra et al. |
| 7,501,048 B2 | 3/2009 | Loermans et al. |
| 2005/0098444 A1 | 5/2005 | Schaeffer |
| 2005/0263171 A1 | 12/2005 | Wu et al. |
| 2005/0288773 A1 | 12/2005 | Glocker et al. |
| 2007/0034527 A1 | 2/2007 | Diaz et al. |
| 2007/0034528 A1* | 2/2007 | Diaz et al. ..................... 205/686 |
| 2007/0209947 A1* | 9/2007 | Shrivastava et al. .......... 205/662 |

FOREIGN PATENT DOCUMENTS

WO WO 2007/103446 9/2007

OTHER PUBLICATIONS

Notification of Transmittal of the International Search Report and the Written Opinion of the International Searching Authority, or the Declaration, Patent Cooperation Treaty, European Patent Office, Dec. 29, 2009 (12 pages).
U.S. Appl. No. 11/370,642, Sep. 22, 2009, Office Action.
U.S. Appl. No. 11/370,642, Apr. 12, 2010, Notice of Allowance.

* cited by examiner

Primary Examiner — In Suk Bullock
Assistant Examiner — Jennifer Wecker
(74) Attorney, Agent, or Firm — Workman Nydegger; John Kwok

(57) ABSTRACT

An electropolishing system including an anode, a cathode, a rolling block and a motion controller. The anode is configured to removably retain a metal device to be electropolished, and may be formed as a bar made from a solid cylindrical piece of metal or other configurations, such as wires with hooks. The anode transfers the electricity to the metal device while grooming the surface of the metal device as it contacts the rolling block. The cathode may be configured as a mesh and completes the electrical circuit. The rolling block is formed from a relatively smooth, solid material and positioned so as to allow the metal device to roll against the surface of the block. The motion controller is configured to provide vertical and horizontal movement of the anode and metal device, using force transducers to control the compression of the metal device against the rolling block.

18 Claims, 6 Drawing Sheets

AUTOMATED ELECTROPOLISHING PROCESS

BACKGROUND OF THE INVENTION

The present invention relates to devices, systems and methods for electropolishing metallic material, and more particularly to an anode/cathode system having a rolling block and unique mandrel configurations.

Medical devices, such as intravascular stents, may be constructed of a metal or polymer and generally cylindrical in shape and hollow, are implanted within the vessel to maintain lumen size. The stent acts as a scaffold to support the lumen in an open position. Configurations of stents include a cylindrical sleeve defined by a mesh, interconnected stents, or like segments. Exemplary stents are disclosed in U.S. Pat. Nos. 4,739,762; 5,133,732; 5,292,33; 5,421,955 and 6,090,127, the contents of which are hereby incorporated herein in their entirety by reference thereto.

One method of making a stent is by using a machine controlled laser to cut a thin walled tubular member, such as stainless steel tubing, to remove portions of the tubing in the desired pattern for the stent, leaving relatively untouched the portions of the metallic tubing that are to form rings or other patterns in the tubing. The stent may be manufactured by direct laser cutting from a single metal tube using a finely focused laser beam passing through a coaxial gas jet structure to impinge on the working surface of the tube as the linear and rotary velocity of the tube is precisely controlled. An exemplary system and process for laser cutting may be found in U.S. Pat. No. 5,759,192, the content of which is hereby incorporated herein in its entirety by reference thereto. Further, other processes of forming stent rings are possible and are known in the art, such as, but not limited to, chemical etching, electronic discharge machining and stamping. An exemplary system and process for chemical etching may be found in U.S. Pat. No. 5,735,893, the content of which is hereby incorporated herein in its entirety by reference thereto.

There is a need for, and what was heretofore unavailable, an automated system and method for electropolishing medical devices, such as laser cut stents. The present invention solves these and other needs.

SUMMARY OF THE INVENTION

The apparatus and method of the present invention are directed to automated electropolishing of metallic material, such as, but not limited to, metal plates, biocompatible medical devices and implants (for example, stents) and dental devices (for example, bridges). The system of the present invention is configured to automate the electropolishing process so as to reduce/eliminate errors or defects due to operator handling while increasing throughput, including eliminating or reducing the need for off-line device grooming and rotation. The mandrels of the present invention are configured to be used in any electropolishing process designed for devices made from stainless steel, cobalt-chromium, nitinol, and/or any other metal or alloy suitable for electropolishing.

The system of the present invention for electropolishing a metal device includes a reservoir for containing an electrolyte solution with a cathode subassembly and a roller plate disposed in the reservoir. The system further includes an anode disposed between the cathode subassembly and the roller plate. The anode being configured to removably retain at least one metal device (such as an implantable medical device) and being operably connected to a positioning subassembly, such as a vertical and longitudinal motion controller. The positioning subassembly includes at least one force transducer, a vertical controller for positioning the anode proximate to the roller plate and a longitudinal controller for moving the anode along the length of the roller plate. The anode may be configured to removably retain one or more stents. The anode may be formed as a mandrel having one or more hooks for single or dual-point contact with the stent, or formed using other mandrel configurations (such as but not limited to a cylindrical rod, coiled mandrel, or a spiral mandrel), all of which may have differing degrees of effectiveness. A second cathode formed from a mesh or rod may be disposed within the lumen of the stent. Alternatively, a non-conducting rod may be used to removably secure the device to be electropolished and the roller plate may be connected to an anodic electrical source.

The method for electropolishing a metal device (such as an implantable medical device) in accordance with the present invention includes providing a reservoir containing an electrolyte solution, a roller plate and a cathode. The process includes connecting the cathode to a source of electricity and providing an anode disposed between the cathode and the roller plate. The anode is connected to a source of electricity and is operably connected to a positioning subassembly. At least one medical device, such as a stent, may be removably secured to the anode. The positioning subassembly is activated so as to engage the medical device with the roller plate and to move the medical device along a longitudinal axis of the roller plate while electric current flows between the anode and the cathode subassembly. After the electropolishing process is completed, the positioning subassembly is further activated so as to disengage the medical device from the roller plate and allow the user to remove the medical device from the anode.

Some of the advantages of the system and method of the present invention over current manufacturing processes may include: (i) the stent is not handled by an operator during the polishing process, thereby eliminating and/or reducing handling defects; (ii) the process is automated, thereby eliminating and/or reducing operator variability while increasing uniformity and consistency; (iii) better control over operating parameters since the applied current can be continuous or pulsed, the devices may not need be removed between polishing cycles; (iv) the stent is in continuous motion, thereby eliminating and/or reducing the need to flip and rotate the stent between cycles, which reduces handling, polishes the stent more uniformly; (v) the stent is continuously groomed, reducing the probability of melted or burned strut defects.

The aforementioned and other features and advantages of the invention will become further apparent from the following detailed description of the presently preferred embodiments, read in conjunction with the accompanying drawings. The detailed description and drawings are merely illustrative of the invention rather than limiting, the scope of the invention being defined by the appended claims and equivalents thereof.

DETAILED DESCRIPTION OF THE INVENTION

Figure 1:
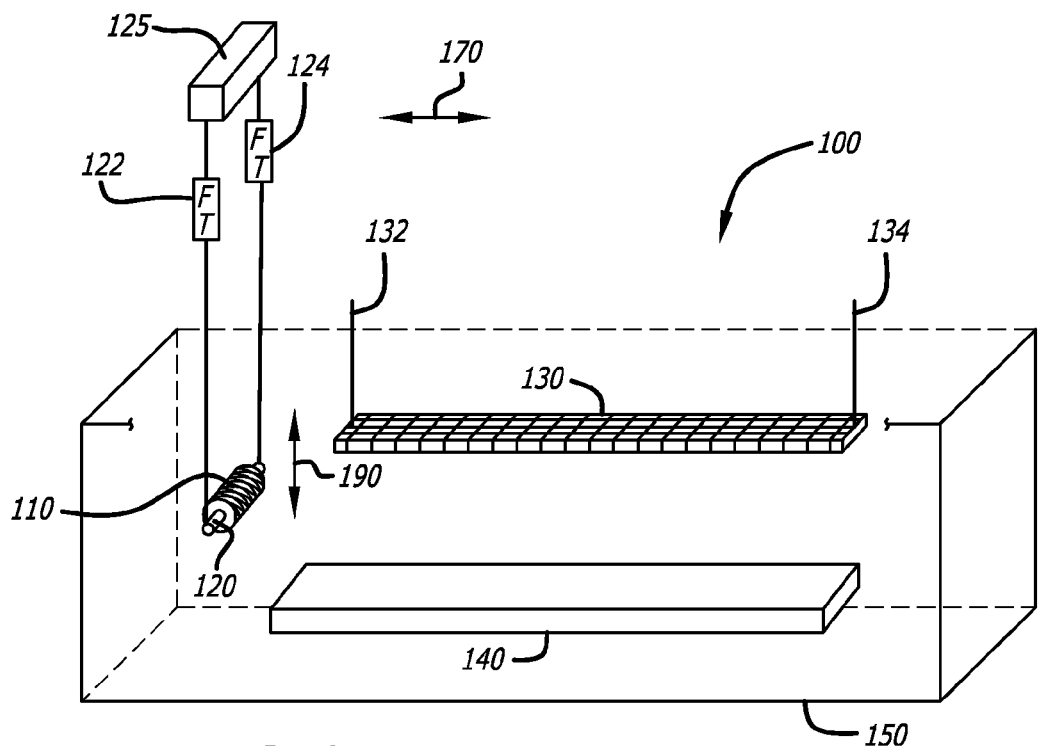
FIG. 1 is a schematic representation depicting the automated electropolishing system of the present invention in the 'loading' position.

The apparatus, system and method of the present invention are configured to automatically groom and polish metallic material in a single electropolishing process. The devices and processes are designed to automate the electropolishing process so as to reduce and/or eliminate errors or defects due to operator handling while increasing throughput, including eliminating or reducing the need for off-line device grooming and rotation. The mandrels of the present invention are configured to be used in a system and process configured for polishing devices made from stainless steel, cobalt-chromium, nitinol and other alloys or metals that are suitable for electropolishing.

In one embodiment, the system of the present invention is designed to electropolish medical devices, such as, but not limited to, stents, dental appliances and other biocompatible metal implants. The system, although not optimal, could use a spiral mandrel typical in prior art electropolishing systems to hold the medical device during the polishing process or to provide the electrical contact between the medical device and the power supply (anodic connection). However, this would require thicker and stiffer spiral mandrels than are currently being used. Instead of the spiral mandrel, a straight rod is placed within the medical device and is used to groom the medical device and provide the electrical connection from the anode (+) power supply (attracts negative ions; repels positively charged ions) through the medical device. In other embodiments, the mandrels are formed with bends, hooks or other configurations to removably engage the medical device. Although the description and figures herein may be specifically directed towards stents, the scope of the present invention is not intended to be limited for use with such medical devices and is applicable to electropolishing any metal structure.

The general components of the stent electropolishing system of the present invention are an anode, a cathode subassembly, a rolling block and a positions subassembly, such as a vertical and longitudinal motion controller. The anode is configured to removably retain the stent (device to be electropolished), and may be formed as a bar made from a solid cylindrical piece of metal. The anode also conducts electricity and transfers the electricity to the stent, while at the same time grooms the surface of the stent as it contacts the rolling block. The cathode subassembly may be configured as a mesh and completes the electrical circuit by providing the electrical connection from the cathode (−) power supply (attracts positively charged ions; repels negatively charged ions). The rolling block (grooming bar) is configured and positioned so as to allow the stent to roll against the surface of the block and may be formed from a relatively smooth, solid piece of polytetrafluoroethylene (PTFE, TEFLON), polyvinylidene fluoride (PVDF, KYNAR) or other material that is resistant to corrosion from the electropolishing solution. The motion controller is configured to provide vertical and horizontal movement of the anode and device to be polished. One or more force meters or transducers may be used to control the tension or compression of the stent against the rolling block. The anode, cathode subassembly and motion controller may be connected to a programmable logic computer (PLC) or computer configured to control the process parameters.

A stent suitable for use with the electropolishing mandrels, systems and methods of the present invention may be configured with a plurality of cylindrical elements connected by connecting members, wherein the cylindrical elements have an undulating or serpentine pattern. The stent, however, can have virtually any pattern suitable for electropolishing. The stent may be made to be either balloon expandable or self-expanding. The stent can be formed from any of a number of materials including, but not limited to, stainless steel alloys, nickel-titanium alloys (the NiTi can be either shape memory or pseudoelastic), tantalum, tungsten, and other biocompatible metal or alloy materials. Such materials of manufacture are known in the art.

The stent may be manufactured by direct laser cutting from a single metal tube using a finely focused laser beam. Other processes of forming stent rings are possible and are known in the art, such as, but not limited to, chemical etching, electronic discharge machining and stamping. After laser cutting, the stent rings may be electrochemically polished in an acidic aqueous solution such as a solution of ELECTRO-GLO #300 (ELECTRO GLO Co., Inc. in Chicago, Ill.), which is a mixture of sulfuric acid, carboxylic acids, phosphates, corrosion inhibitors and a biodegradable surface active agent. Additional suitable electropolishing solutions include various acids, such as, but not limited to, HF, HCl, $HNO_3$, $H_2SO_4$ and Phosphoric Acid ($H_3PO_4$).

Turning now to the drawings, in which like reference numerals represent like or corresponding aspects of the drawings, the automated electropolishing system 100 of the present invention includes a stent 110 or other metal device to be electropolished loaded onto an anode rod (bar) 120 that is contained along with a cathode subassembly 130 and a rolling block (grooming pad) 140 within a housing 150. The housing is configured for retaining an electropolishing solution, and may include inlet and outlet fittings (not shown) for filling and emptying the solution. As shown in FIG. 1, the 'Loading' position of the electropolishing system is configured such that the anode rod is positioned adjacent to (below) the cathode subassembly mesh and adjacent to (above) the rolling block, so as to allow the user to place the stent (or stent assembly, which consists of the stent 110 and the anode rod 120) on the anode.

The anode rod 120 is electrically and mechanically connected to one or more force transducers (FT) 122, 124 that control the amount of pressure that is applied to the stent 110 against the rolling block 140. A motion controller (positioning subassembly) 125 is mechanically and electrically attached to the force transducers and the anode rod. The motion controller provides longitudinal movement 170 of the stent along the rolling block. The motion controller also provides vertical movement 190 of the anode rod to lower the stent against the rolling block and to lift the anode rod away from the rolling block. The force transducers are also connected to an anode power supply (not shown), which applies the electric current through the stent (but not necessarily through the force transducers). The cathode subassembly 130 is suspended above the rolling block and includes connectors 132, 134 to the electrical power supply, which completes the electrical circuit. The electropolishing solution is filled to a level in the housing 150 to cover the rolling block, the cathode mesh, the anode and the stent (in the 'Run' mode).

Figure 2:
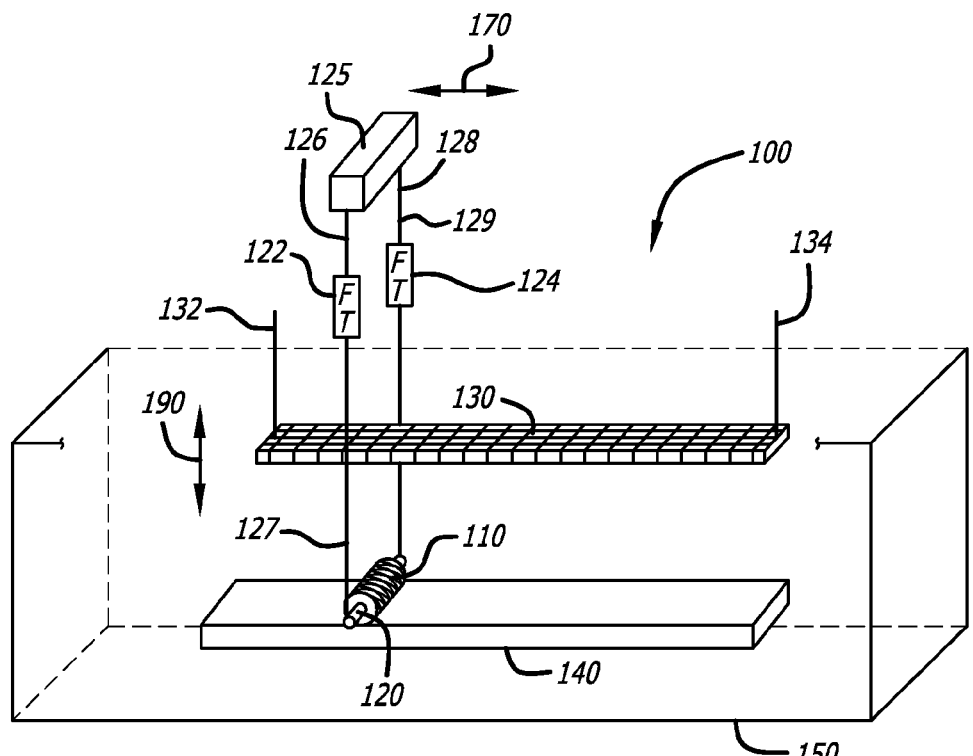
FIG. 2 is a schematic representation depicting the automated electropolishing system of the present invention in the 'run' mode.

After loading the stent on the anode, the automated electropolishing process is continued in the 'Run' mode (FIG. 2). The vertical control of the motion controller 125 lowers the stent 110 onto the rolling block 140 via electrical and mechanical connectors 126, 128. The linear control of the motion controller starts moving (rolling) the stent along the rolling block. The force transducers 122, 124 control the pressure being applied to the stent via electrical and mechanical connectors 127, 129 to the anode rod 120. The anode rod provides the electrical connection between the stent and the anode power supply. The applied force (controlled by the force transducers) continually grooms the stent, and the linear motion rolls the stent so as to continually change the contact point between the stent and the anodic connection.

Figure 3:
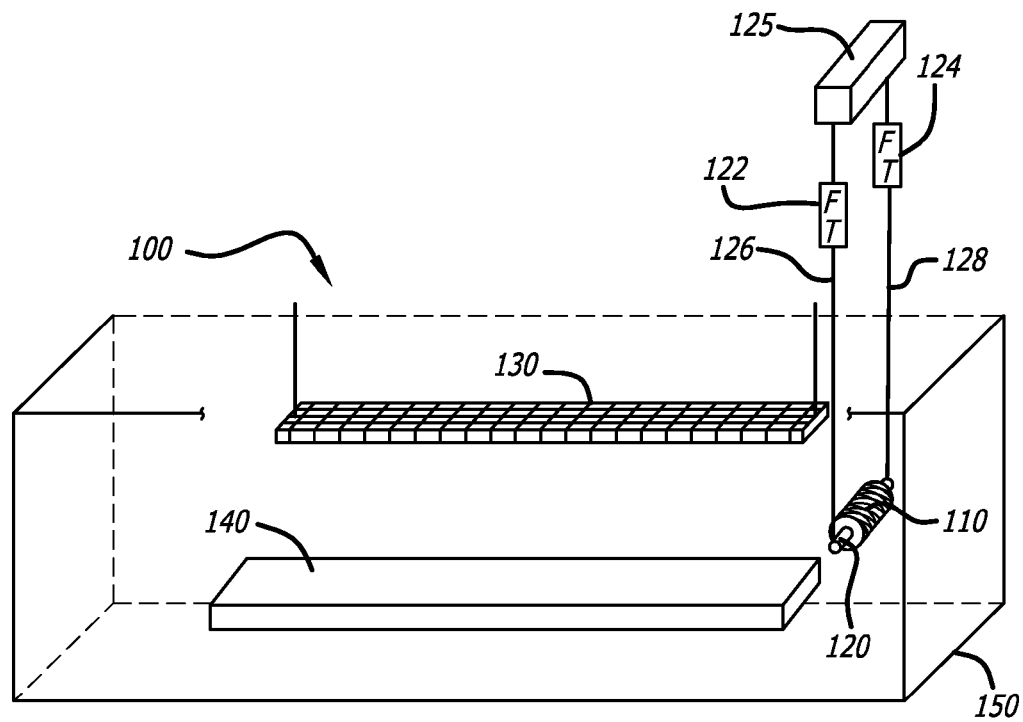
FIG. 3 is a schematic representation depicting the automated electropolishing system of the present invention at the end of a polishing run.

A computer subsystem (not shown), such as a PLC, controls the voltage, current, applied force, linear speed and cycle time for the polishing process. At the end of a polishing run (FIG. 3), the electric current is turned off, and the motion controller 125 moves the stent 110 away from the rolling block 140 and the cathode mesh 130, and lifts the stent out of the polishing solution. The motion controller then 'homes' the device to the 'Start/Load' position (see FIG. 1), a new stent is loaded and the process begins again (see FIG. 2). Since the entire process (excluding loading and removing the stent) is computer controlled, much of the process variation and damage due to operators is eliminated. In addition, the system and method of the present invention should result in a more uniformly polished stent with a lower defect rate and a faster polishing time (overall lower processing time).

Figure 4:
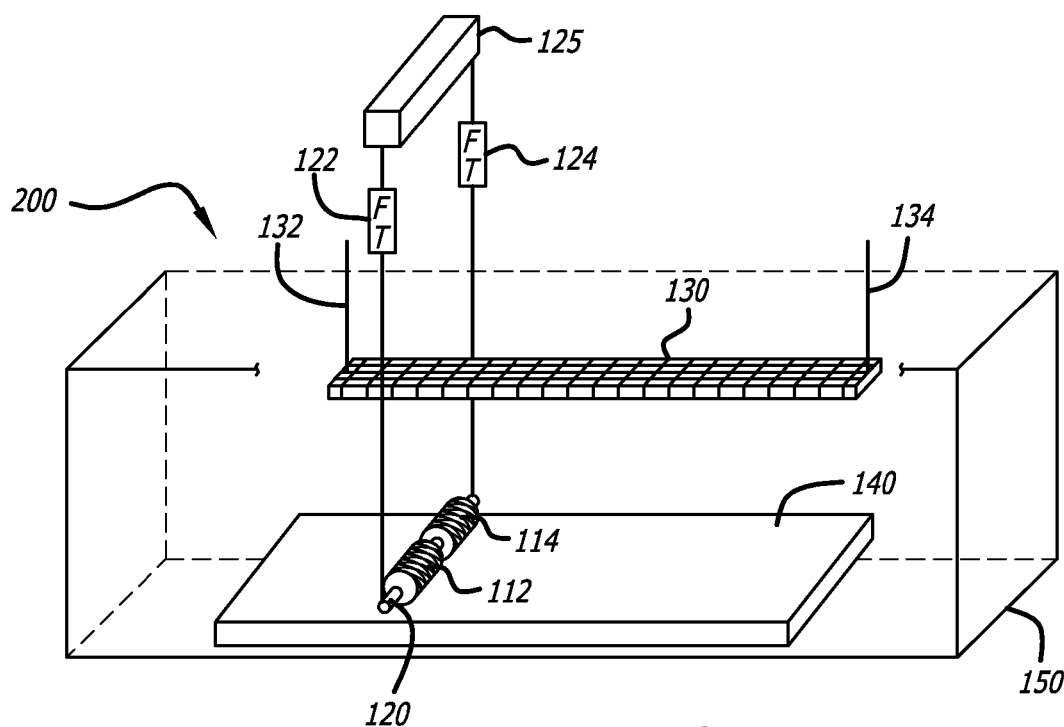
FIG. 4 is a schematic representation depicting the automated electropolishing system of the present invention processing multiple stents.

As shown in FIG. 4, an alternative embodiment of the electropolishing system 200 of the present invention allows for simultaneously processing multiple metal devices (such as two or more stents 112, 114) by configuring the anode rod 120 to removably retain multiple devices. The size and configuration of the rolling block 140 may also be adapted to allow for more than one stent to be polished at one time. The stents are lowered into the polishing solution then compressed against and moved along the rolling block by the motion controller 125 and force transducers 122, 124 while current is applied to the anode rod and cathode mesh 130. This allows continual contact and grooming of the stents, and provides for stent polishing. The computer subsystem controls the current, cycle time, linear speed, tension, and residence time in the bath, which all control surface finish. At the completion of the polishing process, the stents are raised from the bath (FIG. 3) and the system is repositioned to begin polishing the next set of stents.

Figure 5:
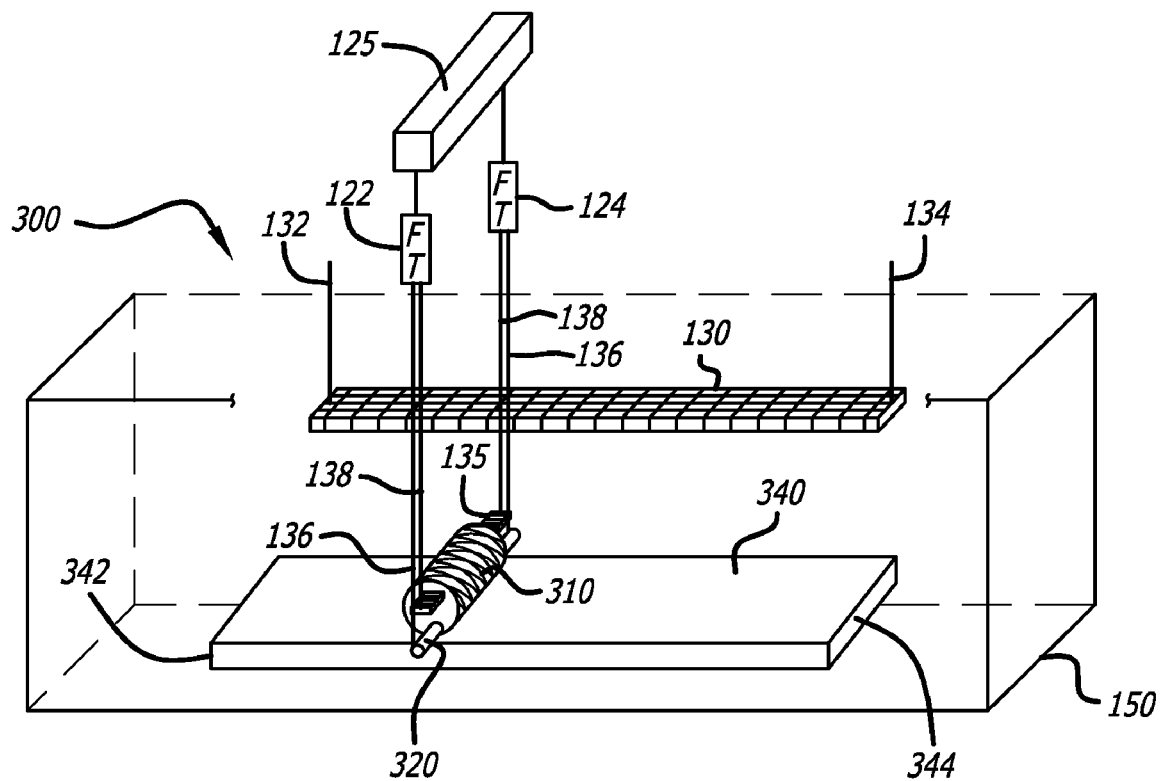
FIG. 5 is a schematic representation depicting an alternative embodiment of the automated electropolishing system of the present invention configured to selectively control and polish the lumen of a metal device.
Figure 6A:
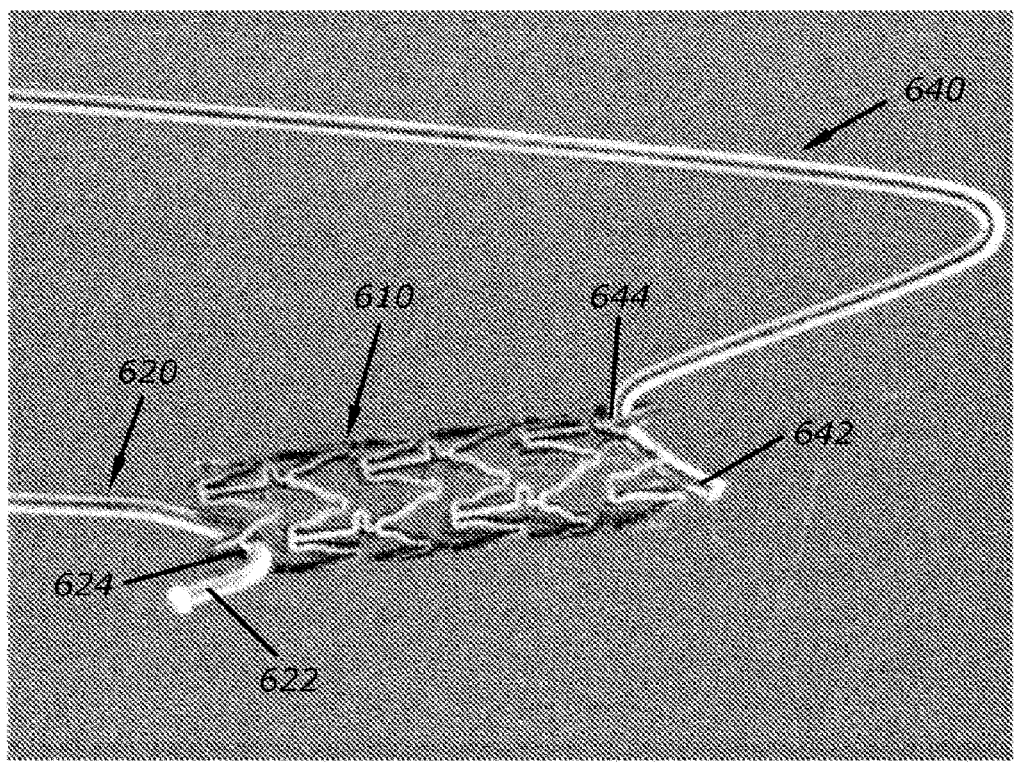
FIG. 6A is a photograph depicting a mandrel of the present invention with a dual-hook design being attached to an unpolished stent.
Figure 6B:
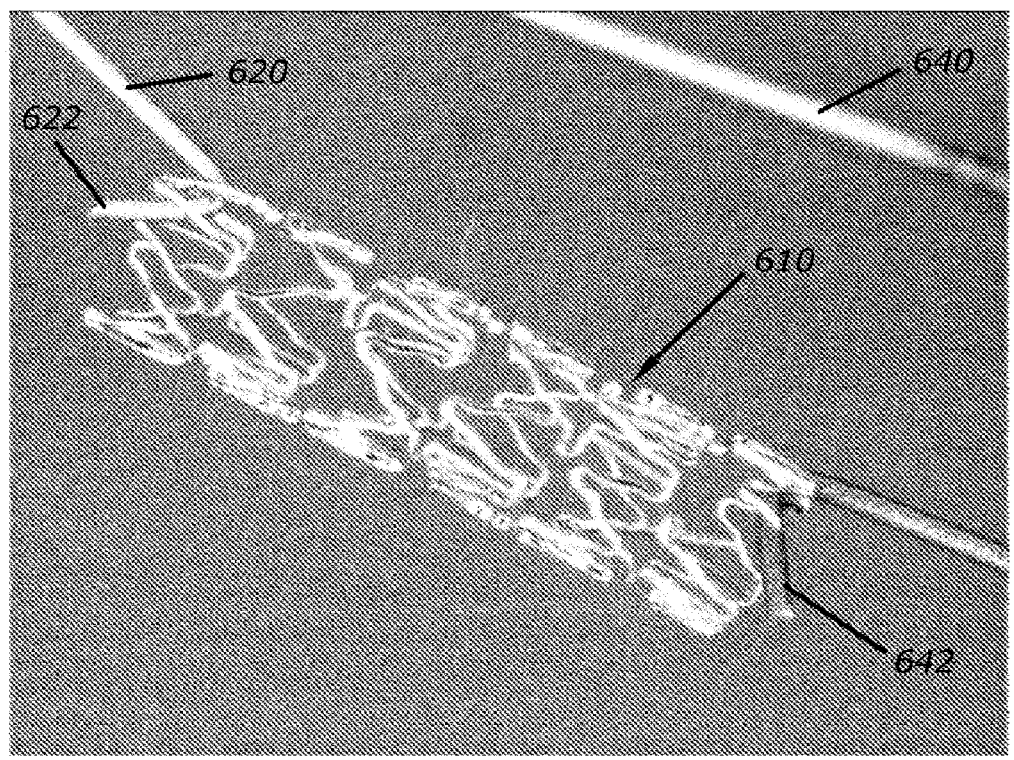
FIG. 6B is a photograph depicting the stent in FIG. 6A after electropolishing with the dual-hook mandrel.

As shown in FIG. 5, a further alternative embodiment of the automated electropolishing system 300 of the present invention is configured to selectively control and polish the lumen of the device(s) to be electropolished, such as a stent 310. A retaining rod 320, which was previously the anode, is formed from a non-conducting material and is configured to removably secure the stent(s). The non-conducting rolling block has been replaced with a conducting metal plate 340, which acts as the anode and includes electrical connections 342, 344. In addition, a second cathode 135 can be attached to or positioned adjacent the non-conducting rod and electrically connected to the motion controller 125. The second cathode may be formed from a fine wire, rod or mesh. The retaining rod applies the pressure of the stent against the rolling block (see FIG. 2), except that the rolling block is now the conducting anode. In this configuration, the polishing of the lumen of the stent can be selectively controlled (as well as the external surface of the stent), which can lead to a smoother inner surface. This allows the lumen of the stent to be polished selectively, since the second cathode is in close proximity to the lumen of the device. In this configuration, the lumen surface may be polished to a finish substantially equal to the exterior surface.

Stent electropolishing is a critical stent in the stent manufacturing process, and is used to convert a laser-cut (or welded) stent into a smoothly polished, highly glossed stent. The electropolishing process can be highly variable; therefore, reducing the variability of the electropolishing process will reduce the variability of the polished stent, which results in a much more uniform finished device. The result is a more consistent product available to the marketplace. One aspect for reducing the electropolishing variability is to redesign the 'spiral mandrel' common in prior art systems. The spiral mandrel is typically a disposable stainless steel spiral wire that is used to hold the unpolished stent and provide for electrical connection during the electropolishing process. The spiral mandrel does an adequate job but has a few shortcomings.

First, the stent is typically over polished (that is defined as more material removed relative to the rest of the stent) at the points of contact between the spiral mandrel and the stent. This results in about one-third of each stent ring (the number of contact points) being 'thinner' than the remainder of the stent.

Second, the spiral mandrel does not adequately polish a stent with variable thickness in the lumen.

Third, the spiral mandrel has to be 'screwed' into the lumen of the stent, which results in handling damage and/or twisting of the stent (accounts for the majority of the defects prior to electropolishing and also during the polishing process for cobalt-chromium stents).

Referring now to FIGS. 6-11, the automated electropolishing system of the present invention includes novel mandrel designs that are configured to electropolish metal devices, such as stents. The mandrels may be formed from stainless steel, platinum, platinum-iridium, nitinol, or any other suitable electo-conducting material. FIG. 6A depicts a reusable dual-hook mandrel attached to an unpolished stent 610. The mandrel includes a first segment 620 having proximal portion connected to an electrical source to form the anode. The distal portion of the mandrel is formed with a first hook or bend 622 that provides a first contact point 624 on the stent. The mandrel includes a second segment 640 having proximal portion connected to the electrical source and a distal portion having a second hook or bend 642 that provides a second contact point 644 on the stent. FIG. 6B shows the stent after electropolishing with the dual-hook mandrel of the present invention.

Figure 7:
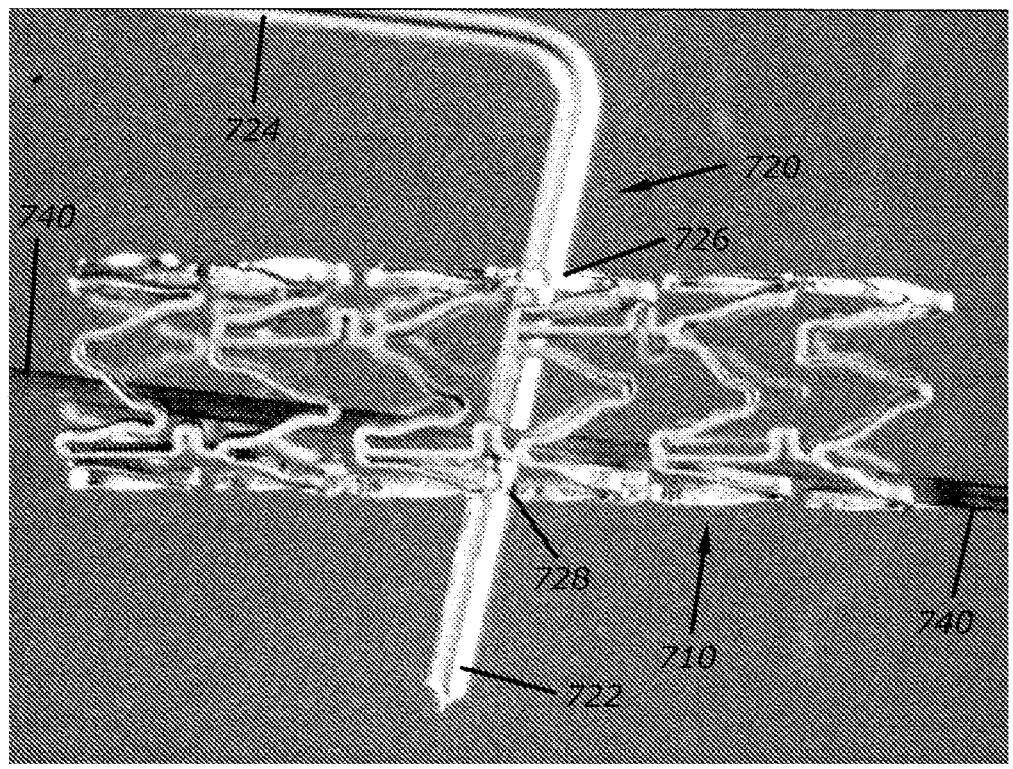
FIG. 7 is a photograph depicting a single-arm, dual point-of-contact electropolishing mandrel in accordance with the present invention.

As shown in FIG. 7, an alternative embodiment of a reusable electropolishing mandrel 720 in accordance with the present invention may be configured with a single distal arm 722 having proximal portion 724 connected to an electrical source to form the anode. The distal portion of the mandrel provides a dual point-of-contact 726, 728 on the stent 710. The stent sidewalls are also polished with this dual point-of-contact design. The stent may be secured in the housing and solution with a non-conducting rod 740.

Figure 8:
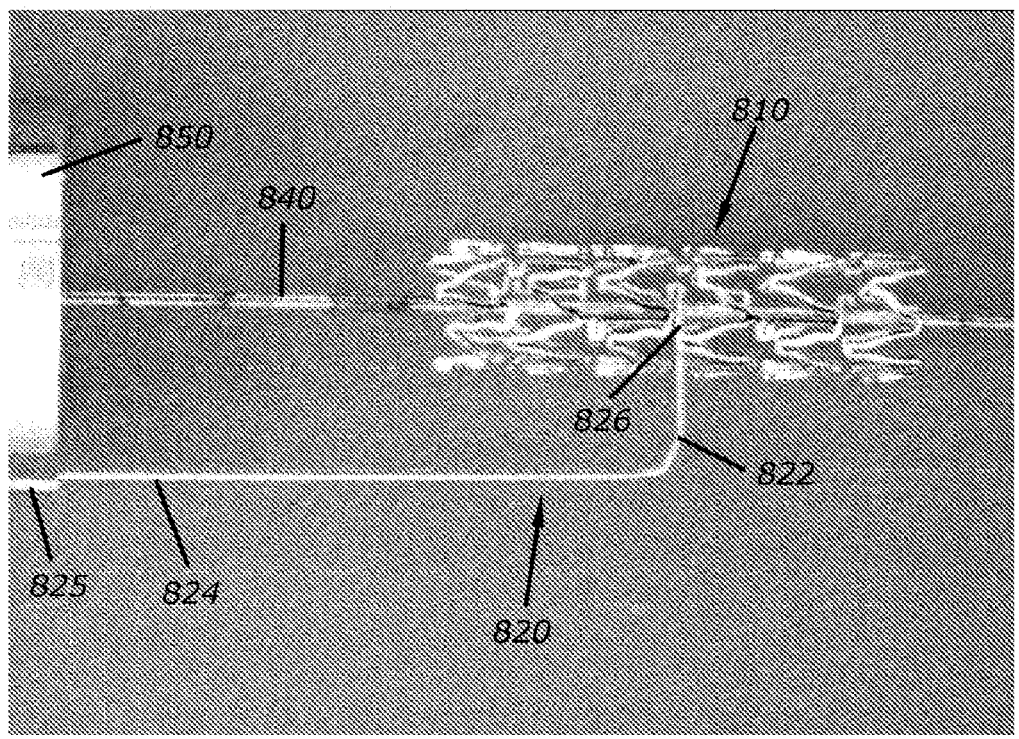
FIG. 8 is a photograph depicting an alternative embodiment of an electropolishing mandrel of the present invention.

Referring to FIG. 8, a further alternative embodiment of a reusable electropolishing mandrel 820 in accordance with the present invention may be configured with a single distal arm 822 having proximal portion 824 connected to an electrical source 825 to form the anode. The distal portion of the mandrel provides a single point-of-contact 826 on the stent 810. The stent may be secured in the housing and solution with a non-conducting rod 840 connected to a fixture 850.

Figure 9:
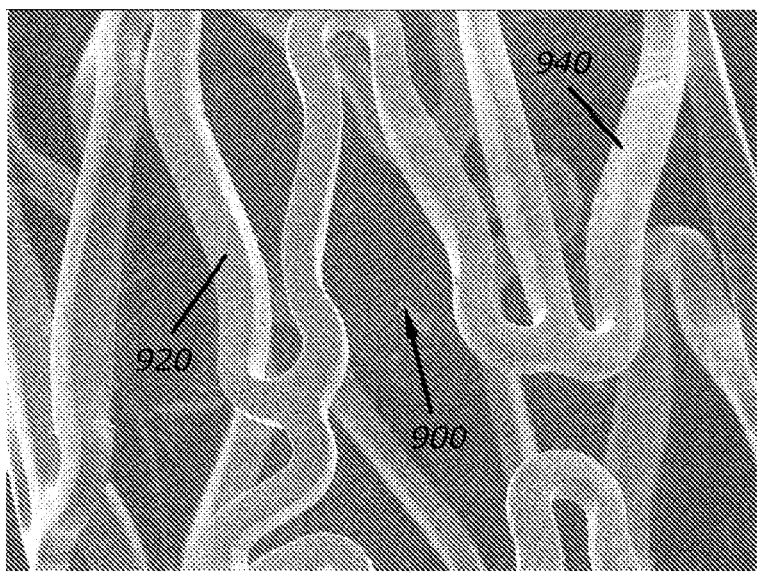
FIG. 9 is a SEM side view image of a stent with variable thickness tubing on the lumen side of the stent that was electropolished using a mandrel of the present invention.
Figure 10:
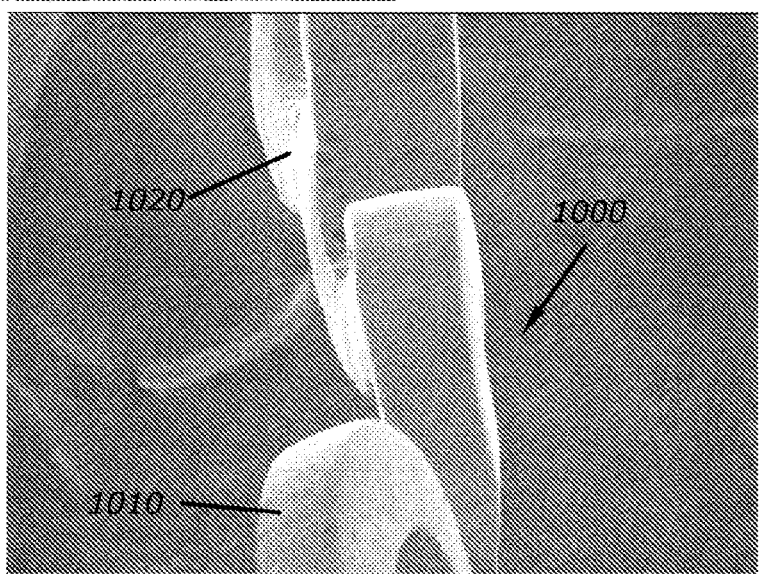
FIG. 10 is a SEM end view of the sidewalls of a stent with variable thickness tubing on the lumen side of the stent that was electropolished using a mandrel of the present invention.
Figure 11:
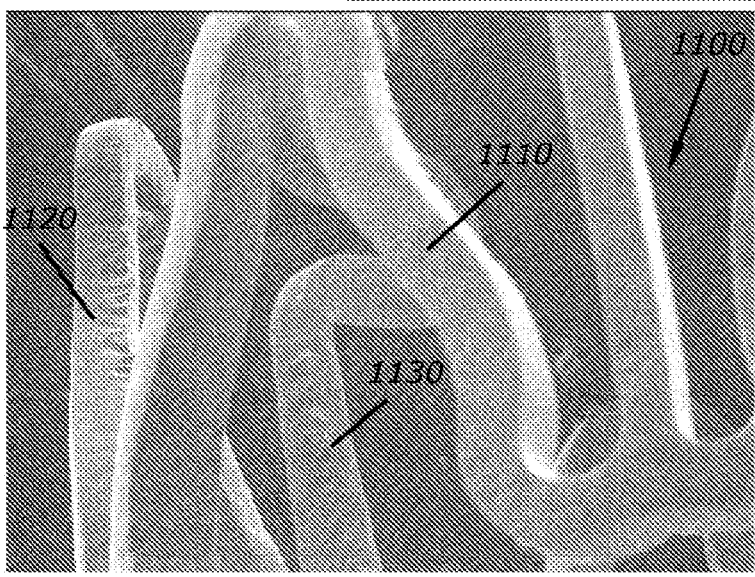
FIG. 11 is a SEM perspective image of a stent electropolished using a mandrel of the present invention.

FIG. 9 is a scanning electron microscope (SEM) image of an eight millimeter (mm) stainless steel stent 900 with variable thickness tubing on the lumen side of the stent. The outside surfaces 920 and inner walls 940 of the stent were adequately electropolished with the mandrel design shown in FIGS. 6A and 6B. As shown in FIG. 10, the lumen walls 1120 and undulations 1110 were adequately polished on the stent 1100. FIG. 11 is an SEM image of a cobalt-chromium stent 1100 electropolished with the mandrel design shown in FIGS. 7 and 8. The outside surfaces 1110, side walls 1120 and lumen walls 1130 of the stent were adequately electropolished.

Some of the advantages of the new mandrel designs in accordance with the present invention are:
- The mandrels are reusable, thus reducing overall manufacturing costs.
- The mandrels work (the stents are electropolished).
- The number of contact points are minimal (usually only two points of contact), which results in less random thinning of struts due to minimizing the number of contact points.
- There are less handling defects because of the ease of use and simplicity of the design.

While particular forms of the present invention have been illustrated and described, it will also be apparent to those skilled in the art that various modifications can be made without departing from the spirit and scope of the invention. Accordingly, it is not intended that the invention be limited, except as by the appended claims.

We claim:

1. A method for electropolishing a medical device, comprising:
    providing a reservoir containing an electrolyte solution and a roller plate;
    providing a cathode and connecting the cathode to a source of electricity;
    providing an anode disposed between the cathode and the roller plate and connecting the anode to a source of electricity, the anode being configured to removably retain a medical device and being operably connected to a positioning subassembly;
    removably securing at least one medical device to the anode;
    activating the positioning subassembly so as to engage the medical device with the roller plate such that the medical device contacts the roller plate;
    causing the positioning subassembly to move the medical device along a longitudinal axis of the roller plate;
    activating the positioning subassembly so as to disengage the medical device from the roller plate; and
    removing the medical device from the anode.

2. The method of claim 1, further comprising providing a positive electric current to the cathode and providing a negative electric current to the anode.

3. The method of claim 1, wherein removably securing at least one medical device to the anode includes attaching at least one stent to the anode.

4. A method for electropolishing a device in an electrolyte solution, the method comprising:
    removably securing at least one device to a mandrel;
    positioning the at least one device against a rolling plate with a positioning assembly;
    moving the at least one device along the rolling plate while current is applied to the at least one device and while the at least one device is immersed in the electrolyte solution; and
    removing the at least one device after the at least one device is electropolished in the electrolyte solution.

5. The method of claim 4, wherein the at least one device includes a medical device and positioning the at least one device against a rolling plate with a positioning assembly includes pressing the at least one device against the rolling plate.

6. The method of claim 5, further comprising controlling an amount of pressure applied to the at least one device against the rolling plate.

7. The method of claim 4, further comprising controlling at least one of:
    a voltage applied to electropolish the at least one device;
    a current applied to electropolish the at least one device;
    a linear speed of moving the at least one device along the rolling plate; or
    a cycle time for electropolishing the at least one device.

8. The method of claim 4, further comprising immersing the at least one device in the electrolytic solution after loading the at least one device on the anode.

9. The method of claim 4, further comprising moving the at least one device along the rolling plate to change a contact point between the at least one device and the anode.

10. The method of claim 4, wherein moving the at least one device includes rolling the at least one device on the rolling plate.

11. The method of claim 10, wherein the mandrel comprises an anode and current is delivered through the anode.

12. The method of claim 10, wherein the mandrel is non-conductive and current is delivered through the rolling plate.

13. The method of claim 10, wherein a cathode is immersed in the electrolytic solution during the electropolishing of the at least one device, further comprising providing a positive electric current to the cathode and providing a negative electric current to the anode.

14. The method of claim 4, wherein removably securing at least one device to the mandrel includes attaching at least one stent to the mandrel.

15. The method of claim 1, further comprising pressing the medical device against the roller plate with the positioning subassembly.

16. The method of claim 15, further comprising controlling an amount of pressure applied to the at least one device against the roller plate.

17. The method of claim 15, further comprising controlling at least one of:
    a voltage applied to electropolish the medical device;
    a current applied to electropolish the medical device;
    a linear speed of moving the medical device along the rolling plate; or
    a cycle time for electropolishing the medical device.

18. The method of claim 15, wherein causing the positioning subassembly to move the medical device along a longitudinal axis of the roller plate includes rolling the medical device on the roller plate.

* * * * *